United States Patent [19]

Levinson et al.

[11] Patent Number: 4,741,901
[45] Date of Patent: May 3, 1988

[54] PREPARATION OF POLYPEPTIDES IN VERTEBRATE CELL CULTURE

[75] Inventors: Arthur D. Levinson, Burlingame; Chung-Cheng Liu, San Bruno; Daniel G. Yansura, San Francisco, all of Calif.

[73] Assignee: Genentech, Inc., South San Francisco, Calif.

[21] Appl. No.: 603,529

[22] Filed: Apr. 24, 1984

Related U.S. Application Data

[63] Continuation of Ser. No. 326,980, Dec. 3, 1981, abandoned, which is a continuation-in-part of Ser. No. 298,235, Aug. 31, 1981, abandoned.

[51] Int. Cl.$^4$ .................. A61K 39/00; A61K 39/12; C12P 21/00; C12P 21/02; C12P 21/04; C12N 15/00; C12N 5/00; C12N 1/00; C07K 13/00

[52] U.S. Cl. .................. 424/88; 424/89; 514/2; 435/68; 435/70; 435/71; 435/172.1; 435/172.3; 435/240.2; 435/320; 530/403; 530/806; 530/826; 935/12; 935/65; 935/70

[58] Field of Search .................. 424/88, 89; 260/112.5 R, 112 R; 536/27; 435/68, 70, 71, 91, 172.3, 240, 241, 243, 253, 317, 235, 236, 172.1, 240.2, 317.1, 320; 935/12, 32, 65, 70; 514/2; 530/403, 350, 806, 826

[56] References Cited

U.S. PATENT DOCUMENTS

| | | | |
|---|---|---|---|
| 3,636,191 | 1/1972 | Blumberg et al. | 424/89 |
| 4,164,565 | 8/1979 | Prince et al. | 935/65 |
| 4,399,216 | 8/1983 | Axel et al. | 435/6 |
| 4,428,941 | 1/1984 | Galibert et al. | 424/177 |
| 4,442,205 | 4/1984 | Hamer et al. | 435/68 |

FOREIGN PATENT DOCUMENTS

| | | | |
|---|---|---|---|
| 0013828 | 8/1980 | European Pat. Off. | 435/172.3 |
| 0020251 | 12/1980 | European Pat. Off. | 435/172.3 |
| 0038765 | 10/1981 | European Pat. Off. | 435/172.3 |
| 0037723 | 10/1981 | European Pat. Off. | 435/172.3 |
| 0062574 | 10/1982 | European Pat. Off. | 435/172.3 |

OTHER PUBLICATIONS

Neurath et al., "Nature" 315: 154–156 (May 9, 1985).
Peter A. Bachman, ed., "Biological Products for Viral Diseases" Munich Symposia on Microbiology, pp. 45–62 and 64–68 (1981).
Dubois et al., "Proc. Natl. Acad. Sci. USA" 77(8): 4549–4553 (Aug. 1980).
Moriarity et al., "Proc. Natl. Acad. Sci. USA" 78(4): 2606–2610 (Apr. 1981).
Charnay et al., "Proc. Natl. Acad. Sci. USA" 76(5): 2222–2226 (May 1979).
Burrell et al., "Nature" 279: 43–47 (May 1979).
MacKay et al., "Proc. Natl. Acad. Sci. USA" 78(7): 4510–4514 (Jul. 1981).
Feitelson et al., "Virology" 130: 76–90 (1983).
Tiollais et al., "Science" 213: 406–411 (Jul. 1981).
Gething et al., "Nature" 293: 620–625 (Oct. 1981).
Mulligan et al., "Nature" 277: 108–114 (Jan. 1979).
Lai et al., "Proc. Natl. Acad. Sci. USA" 77(1): 244–248 (Jan. 1980).
Mantei et al., "Nature" 281: 40–46 (Sep. 1979).
Mulligan et al., "Science" 209: 1422–1427 (Sep. 1980).
Hamer et al., "Nature" 281: 35–40 (Sep. 1979).
Gluzman, "Chemical Abstracts" 94:81818p (1981).
O'Hare et al., "Chemical Abstracts" 94:171851y (1981).
Pribnow, "Biological Regulation and Development", vol. 1, Goldberger, ed., Plenum Press, N.Y., 231–244 (1979).
Valenzuela et al., "Nature" 280: 815–819 (Aug. 1979).
Shepard et al., "DNA" 1(2): 125–131 (1982).

*Primary Examiner*—James Martinell

[57] ABSTRACT

Novel vaccines are provided for immunization against hepatitis B surface antigen wherein the surface antigen is present in 22nm form but contains only mature hepatitis B surface antigen.

1 Claim, 9 Drawing Sheets

B.

SV40 (-VP-1)    ···TCTAAAAGCTTATGAAG[ATG]···
SV40 (-HB$_S$Ag) ···TCTAAAAGCTGAATTC[ATG]···

RECOMBINANT SV40-HBV DNA REPLICATES IN CV-1 CELLS

PREPARATION OF POLYPEPTIDES IN VERTEBRATE CELL CULTURE

CROSS REFERENCE TO RELATED APPLICATION

This is a continuation of U.S. Ser. No. 326,980, filed Dec. 3, 1981, now abandoned, which in turn is a continuation-in-part of U.S. Ser. No. 298,235, filed Aug. 31, 1981 and now abandoned.

FIELD OF THE INVENTION

This invention relates to the application of recombinant DNA technology for the production of polypeptides in vertebrate cell culture. In one aspect, the present invention relates to the construction of expression vehicles containing DNA sequences encoding polypeptides operably linked to expression effecting promoter systems and to the expression vehicles so constructed. Such expression vehicles are capable of replication and of expression of the encoded polypeptide DNA sequence in both microbial systems and, notably, in various vertebrate cell culture systems. In another aspect, the present invention relates to vertebrate cell cultures transformed with such expression vehicles, thus directed in the expression of the DNA sequences referred to above.

In preferred embodiments, this invention provides for particular expression vectors that utilize DNA sequences for replication, phenotypic selection and linking to the hepatitis B surface antigen (HBsAg) gene and expression promoter therefor which sequences are natural to and not detrimental in the host vertebrate cell system employed. The HBsAg is secreted into the culture medium in particle form of about 22 nm and contains antigenic determinant(s) of hepatitis B virus (HBV). The thus produced hepatitis B surface antigen is suitable for use in the preparation of vaccines against hepatitis B virus and this invention also relates to the means and methods of converting the end product HBsAg of such cell culture expression to entities, such as vaccines, useful against HBV.

The publications and other materials hereof used to illuminate the background of the invention, and in particular cases, to provide additional details respecting its practice are incorporated herein by reference, and for convenience, are numerically referenced in the following text and respectively grouped in the appended bibliography.

BACKGROUND OF THE INVENTION

A. Recombinant DNA Technology

With the advent of recombinant DNA technology, the controlled microbial production of an enormous variety of useful polypeptides has become possible. Many vertebrate polypeptides, such as human growth hormone, human proinsulin, desacetylthymosin alpha 1, human and hybrid leukocyte interferons, human fibroblast interferon, as well as a number of other products have already been produced by various microorganisms. The power of the technology admits the microbial production of an enormous variety of useful polypeptides, putting within reach the microbially directed manufacture of hormones, enzymes, antibodies, and vaccines useful for a wide variety of drug-targeting application.

A basic element of recombinant DNA technology is the plasmid, an extrachromosomal loop of double-stranded DNA found in bacteria oftentimes in multiple copies per cell. Included in the information encoded in the plasmid DNA is that required to reproduce the plasmid in daughter cells (i.e., a "replicon" or origin of replication) and ordinarily, one or more phenotypic selection characteristics, such as resistance to antibiotics, which permit clones of the host cell containing the plasmid of interest to be recognized and preferentially grown in selective media. The utility of bacterial plasmids lies in the fact that they can be specifically cleaved by one or another restriction endonuclease or "restriction enzyme", each of which recognizes a different site on the plasmid DNA. Thereafter heterologous genes or gene fragments may be inserted into the plasmid by endwise joining to the cleavage site or at reconstructed ends adjacent to the cleavage site. Thus formed are so-called replicable expression vehicles.

DNA recombination is performed outside the host organism, and the resulting "recombinant" replicable expression vehicle, or plasmid, can be introduced into the cells of organisms by a process known as transformation and large quantities of the recombinant vehicle obtained by growing the transformant. Moreover, when the gene is properly inserted with reference to portions of the plasmid which govern the transcription and translation of the encoded DNA message, the resulting expression vehicle can be used to direct the production of the polypeptide for which the inserted gene codes, a process referred to as expression.

Expression is initiated in a DNA region known as the promoter. In the trancription phase of expression, the DNA unwinds, exposing it as a template for initiated synthesis of messenger RNA from the DNA sequence. The messenger RNA is, in turn, bound by ribosomes where the messenger RNA is translated into a polypeptide chain having the amino acid sequence encoded by the mRNA. Each amino acid is encoded by a nucleotide triplet or "codon" which collectively make up the "structural gene", i.e., that part of the DNA sequence which encodes the amino acid sequence of the expressed polypeptide product. Translation is initiated at a "start" signal (ordinarily ATG, which in the resulting messenger RNA becomes AUG). So-called stop condons define the end of translation, and hence, the production of further amino acid units. The resulting product may be obtained by lysing, if necessary, the host cell, in microbial systems, and recovering the product by appropriate purification from other proteins.

In practice, the use of recombinant DNA technology can express entirely heterologous polypeptides---so-called direct expression--or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment. See British Pat. Publ. No. 2007676A and Weszel, *American Scientist* 68, 664 (1980).

If recombinant DNA technology is to fully sustain its promise, systems must be devised which optimize expression of gene inserts, so that the intended polypeptide products can be made available in controlled environments and in high yields.

B. CELL CULTURE TECHNOLOGY

The art of cell or tissue cultures for studing genetics and cell physiology is well established. Means and methods are in hand for maintaining permanent cell lines, prepared by successive serial transfers from isolate normal cells. For use in research, such cell lines are maintained either on a solid support in liquid medium, or by growth in suspension containing support nutriments. Scale-up for large preparations seems to pose only mechanical problems. For further background, attention is directed to *Microbiology*, 2nd Edition, Harper and Row Publishers, Inc. Hagerstown, Maryland (1973) especially pp. 1122 et seq. and *Scientific American* 245. 66 et seq. (1981), each of which is incorporated herein by this reference.

SUMMARY OF THE INVENTION

The present invention is based upon the discovery that recombinant DNA technology can be used to successfully and efficiently produce polypeptides in any vertebrate host cell culture system and thus carries the advantages such systems confer, to wit, glycosylation, phosphorylation, methylation and sugar and lipid association more closely related to animal proteins naturally produced versus their production in bacterial or even yeast hosts which are incapable of such level of sophisticated processing. In addition, the vertebrate cell cultures no doubt will tolerate the polypeptide product well and notably can, in some cases, secrete the product into the cell culture medium, immeasurably aiding in the recovery and purification methods.

The present invention comprises the polypeptides thus produced and the methods and means of their production. The present invention also is directed to replicable expression vehicles harboring DNA sequences encoding polypeptides in directly expressable form when disposed within vertebrate cell cultures. Further, the present invention is directed to vertebrate cell cultures transformed with the expression vehicles described above, capable of expressing such polypeptides. In still further aspects, the present invention is directed to various processes useful in preparing such DNA sequences, DNA expression vehicles and cultures and to specific embodiments thereof. Still further, this invention is directed to the use of thus produced polypeptides for administration in the treatment of various disease/conditions in mammals and for making pharmaceutical or animal health compositions suitable for such treatment.

DESCRIPTION OF PREFERRED EMBODIMENT

In one preferred embodiment, the present invention is directed to means and methods of producing in vertebrate cell culture, hepatitis B surface antigen (HBsAg) in discrete particle form comprising immunogenic determinant(s) of hepatitis B virus (HBV). The HBsAg hereof is secreted into the cell culture medium in discrete particle form, devoid of any additional, fused polypeptide artifact, whether encoded by another portion of the HBV genome or by DNA homologous to the vector employed. This invention contemplates the use of the thus produced HBsAg for the preparation of vaccines useful to confer immunogenicity to HBV in susceptible humans, to such vaccines and to the method of using them to inoculate and confer immunogenicity to HBV in susceptible humans.

HEPATITIS B VIRUS

Hepatitis B (serum hepatitis) virus is transmitted among humans and manifests as chronically debilitating infections which can result progressively in severe liver damage, primary carcinoma and death. In most cases, complete recovery from hepatitis B infections can be expected: however, large segments of the population, especially in many African and Asian countries, are chronic carriers with the dangerous potential of transmitting the disease pandemically.

Hepatatis is caused by a virus vector (hepatitis B virus or HBV) which in its whole state—the so-called Dane particle—represents the virion and consists of a 27nm nucleocapsid enclosing a DNA molecule and an envelope surrounding the nucleocapsid. Proteins associated with the virion include the core antigen (HBcAg), a DNA polymerase and the surface antigen (HBsAG) which has been found in serum of infected and carrier humans. Antibodies to HBsAG have also been found in serum HBV infected people. It is believed that HBsAG is the HBV antigen that can induce immunogenic production of antibody (anti-HBs) and thus it would be the principal in an HBV vaccine. Attention is directed to: Dane et al., *Lancet* 1970 (I), 695 (1970); Hollinger et al., *J. Immunology* 107, 1099 (1971); Ling et al., *J. Immunology* 109, 834 (1972); Blumberg, Science 197, 17 (1977); Peterson et al., *Proc. Nat. Acad. Sci (USA)* 74, 1530 (1977) and *Viral Hepatitis, A Contemporary Assessment of Etiology, Epidemiology, Pathogenesis and Prevention.* (Vyas et al., eds.) Franklin Institute Press, Philadelphia, 1978, each of which is hereby incorporated by this reference to further illustrate the background of this invention.

HBsAg is present in infected plasma predominantly in the form of spherical particles having diameters ranging from about 16 to 25 nm—the so-called "22 nm particle." These are thought to represent a noninfectious viral envelope. Because antibodies against HBsAg are protective against HBV infection, these non-infectious particles can effectively be used as a vaccine.

Inasmuch as the hepatitis B virus has not been infectious in cell culture and can only be obtained from infected humans or higher primates, means have not been available for obtaining and maintaining sufficient supplies of HBV for use in producing antigen for immunization against HBV.

STATE OF THE ART

In British Patent Application Publication No. 2034323A and European Patent Applications Publications Nos. 13828 and 20251 are respectively described the isolation and cloning of the HBV genome, the expression of HBV core antigen and the production in *E. coli* of a fusion protein puportedly containing a portion of HBsAg. *Proc. Natl. Acad. Sci. (USA)* 77, 4549 (1980) reports the integration of mouse chromosome by transformation of mouse cells with tandem cloned hepatitis B genomes.

Moriarty et al., in *Proc. Natl. Acad. Sci. (USA)* 78, 2606 (1981), describe the construction of a simian virus 40 (SV40) recombinant carrying a fragment of HBV-DNA. Cultures of monkey kidney cells were infected with the viral recombinant and produced a 22 nm particle purportedly characteristic of those found in sera of hepatitis B infected patients. The Moriarty et al. recombinant vector contained a large segment of the HBV genome harboring the HBsAg sequence and included DNA sequences encoding SV40 tumor proteins and possibly other HBV proteins.

Further, their construction incorporated the HBsAg DNA in frame with the VP-2 protein coding sequence of SV40 virus. It is not clear whether mature HBsAg was expressed.

CELL CULTURE SYSTEMS/CELL CULTURE VECTORS

Figure 1:
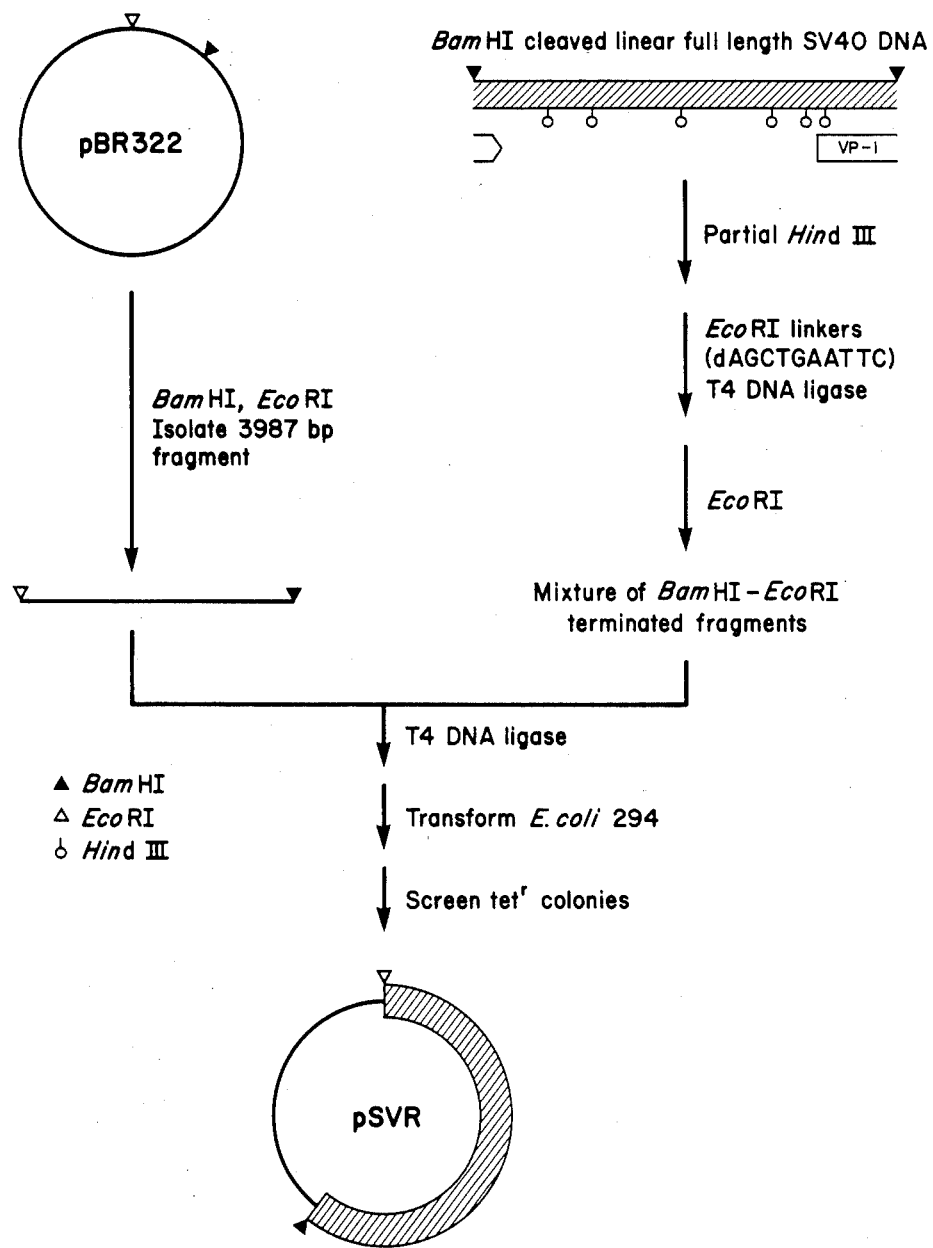
FIG. 1 depicts the construction of plasmid pSVR containing SV40 DNA with a deletion of the coding region for the VP-1 protein.

Propagation of vertebrate cells in culture (tissue culture) has become a routine procedure in recent years (see *Tissue Culture*, Academic Press, Kruse and Patterson eds, 1973). Employed herein was the CV-1 line of monkey kidney fibroblasts as the host for the production of HBsAg. However, the experiments detailed here could be performed in any cell line which is capable of the replication and expression of a compatible vector. e.g., WI38, BHK, 3T3, CHO, VERO, and Hela cell lines. Additionally, what is required of the expression vector is an origin of replication and a promoter located in front of, and in reading phase with, the gene to be expressed, along with any necessary ribosome binding sites, RNA splice sites, polyadenylation site, and transcriptional terminator sequences. While these essential elements of SV40 have been exploited, it will be understood that the invention, although described herein in terms of a preferred embodiment, should not be construed as limited to these sequences. For example, the origin of replication of other viral (e.g., Polyma, Adeno, Retro, VSV, BPV, and so forth) vectors could be used, as well as cellular origins of DNA replication which could function in a non-integrated state.

In addition, the replication of SV40 DNA begins at a unique site and proceeds bidirectionally (19). Genetic evidence indicates that only one viral gene product is required for the replication of the viral DNA. This is the product of the A gene (T antigen), which is required to initiate each round of viral DNA synthesis (12). Experiments described herein have demonstrated that recombinant plasmids containing the origin of DNA replication of SV40 are able to replicate in monkey cells in the presence of SV40 large T antigen (20, 21). It was desired to construct vectors which preserved both replication and promoter functions. That such a system can be employed to express heterologous genes in the absence of a complementing helper virus also has been established.

POLYPEPTIDE PRODUCTS

The present invention is useful for the preparation of a wide variety of polypeptides exhibiting bioactivity akin to that of a polypeptide innately produced within a living organism for a physiological purpose, as well as to intermediates which can be processed into such polypeptides, as by cleavage away of superfluous protein, folding, combination etc. Examples are hormones, e.g., human growth hormone, bovine growth hormone, etc.; lymphokines; enzymes, e.g., superoxide dismutase, etc.; interferons, e.g., human fibroblast and human and hybrid leukocyte interferons, etc.; viral antigens or immunogens, e.g., foot and mouth disease antigens, influenza antigenic protein, hepatitis core and surface antigens, etc.; and various other polypeptides, e.g., human insulin, ACTH, various glycoproteins, immunoglobins, vitamin K requiring blood factors, such as Factor VIII and IX, etc.

The expression vectors hereof effectively direct the synthesis of heterologous polypeptides, inter alia in the COS-7 line of monkey cells. The use of both the early and late promoters of SV40 have been exploited, although other promoters should be useful in this regard. In addition to the efficient expression of potentially useful polypeptides (e.g. growth factors, lymphokines, viral antigens, interferons), the system should be useful in other regards. For example, significant levels of RNA are synthesized from these vectors, indicating that a genomic insert containing introns should generate significant levels of processed RNA from which cDNA clones could be readily obtained. Thus, the system should prove useful for converting genomic inserts into cDNA clones. In addition, in the non-lytic expression system, it should be possible to use this approach to express genes for which a selection pressure can be exerted (e.g. dihydrofolate reductase, thymidine kinase, drug resistance genes, oncogenes) with the aim of obtaining both vectors which rely on host, rather than viral, origins of DNA replication, as well as vectors which replicate stably, perhaps through an acquisition of host sequences (e.g. centromeres).

DETAILED DESCRIPTION

Construction of a SV40 DNA Without The Coding Region of VP-1 Protein

The complete nucleotide sequence of SV40 DNA is known (1), therefore, the physical locations of various SV40 coded proteins can be correlated directly with various restriction enzyme cleavage sites. Examination of the nucleotide sequence encompassing the coding region of VP-1 protein (1) indicated two well placed restriction endonuclease cleavage sites. (FIG. 1). The first is a cleavage site of restriction endonuclease HindIII at nucleotide position 1493, 6 nucleotides 5' to the initiation codon for VP-1 protein. The second, a cleavage site for restriction endonuclease BamHI at nucleotide 2533, is 50 nucleotides 5' to the termination codon for VP-1 protein. To obtain SV40 DNA with deletion between HindIII site at 1493 and BamHI site at 2533, experiments were carried out as outlined in FIG. 1. Briefly, wild type SV40 DNA was first cleaved with BamHI to obtain a full-length linear DNA and then cleaved with HindIII under the condition that each DNA molecule, on average, received only one cleavage (there are six HindIII cleavage sites distributed throughout the SV40 genome). In theory, one out of twelve of the resulting digested DNA mixture should be the one combination desired. Subsequently, a synthetic decanucleotide, dAGCTGAATTC (2), was ligated to these BamHI and HindIII treated SV40 DNA through cohesive ends of HindIII cleavage sites (-TCGA) and that of decanucleotides. The whole mixture was then digested with EcoRI (to generate cohesive end in the EcoRI site on the added decanucleotide) and cloned into the pBR322 through Bam and EcoRI (3) sites. The plasmid DNA containing SV40 sequences was screened by restriction analysis (4) and that fragment with the stipulated deletion was isolated and designated as pSVR.

There are two purposes for the addition of synthetic decanucleotide. First, the added decanucleotide contains a cleavage site for restriction endonuclease EcoRI which is absent in this part of SV40 DNA. Therefore, large quantities of this SV40 DNA vector fragment can be readily obtained by the propagation of pSVR plasmid in E. coli (5) and subsequent cleavage with endonuclease EcoRI and BamHI. Secondly, the added decanucleotide will restore the original physical distance between the HindIII cleavage site and initiation codon for VP-1 protein when a properly constructed DNA containing the coding sequences of a foreign gene is ligated to this SV40 DNA through the EcoRI cleavage site (See FIG. 3B).

Eight μg of BamHI cleaved linear full-length SV40 viral DNA (this can be obtained by cleaving wild type SV40 viral DNA or SV40 DNA cloned at the BamHI site of pBR322 with BamHI) was digested with 2 units of Hind III (BRL) in a 60 μl reaction mixture containing 20 mM tris-Cl (pH 7.5), 60 mM NaCl and 7 mM $MgCl_2$. After incubation at 37° C. for 30 minutes, the reaction was stopped by the addition of excess EDTA and the reaction mixture was deproteinized by phenol extraction followed by ethanol precipitation. The partially digested DNA was then resuspended in 10 μl of TE buffer (10 mM tris-Cl, pH 7.5, 1 mM EDTA).

For converting the Hind III site cohesive end to the EcoRI site cohesive end, 0.1 n mole of synthetic decanucleotide dAGCTGAATTC was first phosphurylated with ATP by T4 polynucleotide kinase in 10 μl reaction mixture containing 50 mM glycine buffer (pH 9.1), 10 mM $MgCl_2$, 5mM DTT, 0.5 mM ATP and 10 units of kinase. Incubation was at 37° C. for 1 hour. An aliquot (3 μl) of the kinase reaction mixture was then added to a ligation mixture (20 μl) containing 66 mM tris-Cl (pH 7.5), 6.6 mM $MgCl_2$, 10 mM DTT, 0.05 mg/ml BSA, 0.5 mM ATP, 4 μg of partially Hind III digested SV40 DNA (above) and 10 units of T4 DNA ligase. Incubation for the ligation reaction was at 20° C. for approximately 16 hours.

After the ligated DNA was treated with restriction endonuclease EcoRI to generate EcoRI cohesive end on the ligated linker, it was then deproteinized with phenol, precipitated with ethanol, ligated to the BamHI-EcoRI fragment of PBR322 (0.5 μg) in a 15 μl ligation mixture (see above) and used to transform E. coli 294. Plasmids isolated from these transformants were then screened for the insertion of proper SV40 DNA fragments by various restriction enzyme digestion.

ISOLATION OF HBSAG STRUCTURAL GENE

The above constructed SV40 vector was designed to express the gene encoding the surface antigen of hepatitis B virus (HBsAg). The HBsAg, a polypeptide of 25,000 molecular weight, normally exists as a complex particulate structure (22 nm particle) which is partly glycosylated and is secreted to the exterior of the infected liver cell (6).

For expressing HBsAg in the above constructed SV40 vector, an ideal DNA fragment containing the coding sequence of HBsAg would conform to the following conditions. First, this DNA has EcoRI restriction site on one end and BamHI site on the other. Secondly, the EcoRI site is located immediately 5' to the initiation codon for the HBsAg so that the original position of ATG in the VP-1 protein can be restored. Finally, the resultant recombinant SV40 molecule should be similar in size to wild type SV40 DNA for efficient packaging into viral particles. To meet above conditions, a series of experiments detailed in FIG. 2 were carried out. One of the important features for this construction is the creation of an EcoRI restriction site immediately 5' to the presumed initiation codon (ATG) of HBsAg. This was done by using a synthetic 12-mer (dATGGAGAACATC), which is the sequence corresponding to the initiation codon and those of the following 3 amino acids in the HBsAg, as a site specific primer for E. coli DNA polymerase to synthesize DNA from single-stranded cloned HBV DNA. After proper enzymatic treatment, the synthetic DNA was then spliced with the cloned HBV DNA to reconstitute an intact HBsAg gene, and a treated vector DNA containing an EcoRI site on the end to reconstitute the stipulated EcoRI site. The plasmid is designated pHS94.

The structural gene coding for the HBsAg was recovered from a plasmid (pHBV-7-1A) containing the entire genome of HBV cloned into the EcoRI site of pBR322. This clone was obtained by methods similar to those recently published by Valenzuela et al. (7) and (8).

The structural gene was modified in two ways (1) to incorporate a unique restriction site directly in front of the initial ATG methionine codon and (2) to blunt-end ligate the HBV Hpa I site located distal to the HBsAg gene to the filled in EcoRI site of pBR322. These two modifications to the DNA fragment containing the HBsAg structural gene were accomplished as described below:

1. 50 μg of pHBV-T-IA DNA was first digested with Hpa II (80 units) in 200 μl reaction mixture according to enzyme supplier's (BRL) reaction condition to obtain a 1.7 kb DNA fragment, in which the initiation codon for the coding sequences of HBsAg was located close to the 5' end of the sense-strand (about 400 bp). The DNA was purified by electrophoresis on polyacrylamide gels. (PAGE). The purified HpaII fragment was then treated with λ exonuclease (2 units) in 100 μl reaction mixture (New England BioLab) for 30 minutes at 37° C. λ exonuclease is a 5' exonuclease which digests double stranded DNA. This reaction degraded the 5' half of the "sense-strand" DNA from HBsAg coding sequences and exposed the antisense strand for pairing with added primer. The λ exonuclease treated DNA was deproteinized and resuspended in 50 μl of reaction mixture containing 40 mM potassium phosphate buffer (pH 7.4), 1 mM DTT, 50 μg/ml BSA, 6mM MgCl12, 0.5 mM each of dNTPs, and 0.2 n mole od dATGGAGAAC-TACTC ($^{32}$p-labelled at 5' end by polynucleotide kinase). The mixture was first heated at 90° C. for 1 minute, annealed at 0° C. for 30 minutes and then incubated at 37° C. for 3 hours in the presence of 2 units of E. Coli DNA polymerase I klenow fragment (9). The DNA polymerase synthesized DNA primed by the added primer and degraded single-stranded DNA with 3'-OH termini and, therefore, created blunt ended DNA molecules. The resultant DNA was then deproteinized, digested with XbaI (45 units) at a site located within the HBsAg gene in a 100 μl reaction mixture and fractionated by PAGE. A 91 base pair DNA fragment containing the first 30 codons of HBsAg gene was isolated after autoradiographic detection (fragment A).

To create a unique restriction site site immediately 5' to the HBsAg gene, we took advantage of a derivative of the plasmid pBR322 (called pNCV) which contains a synthetic DNA segment with the sequence:

AATTCTGCAG

Figure 2:
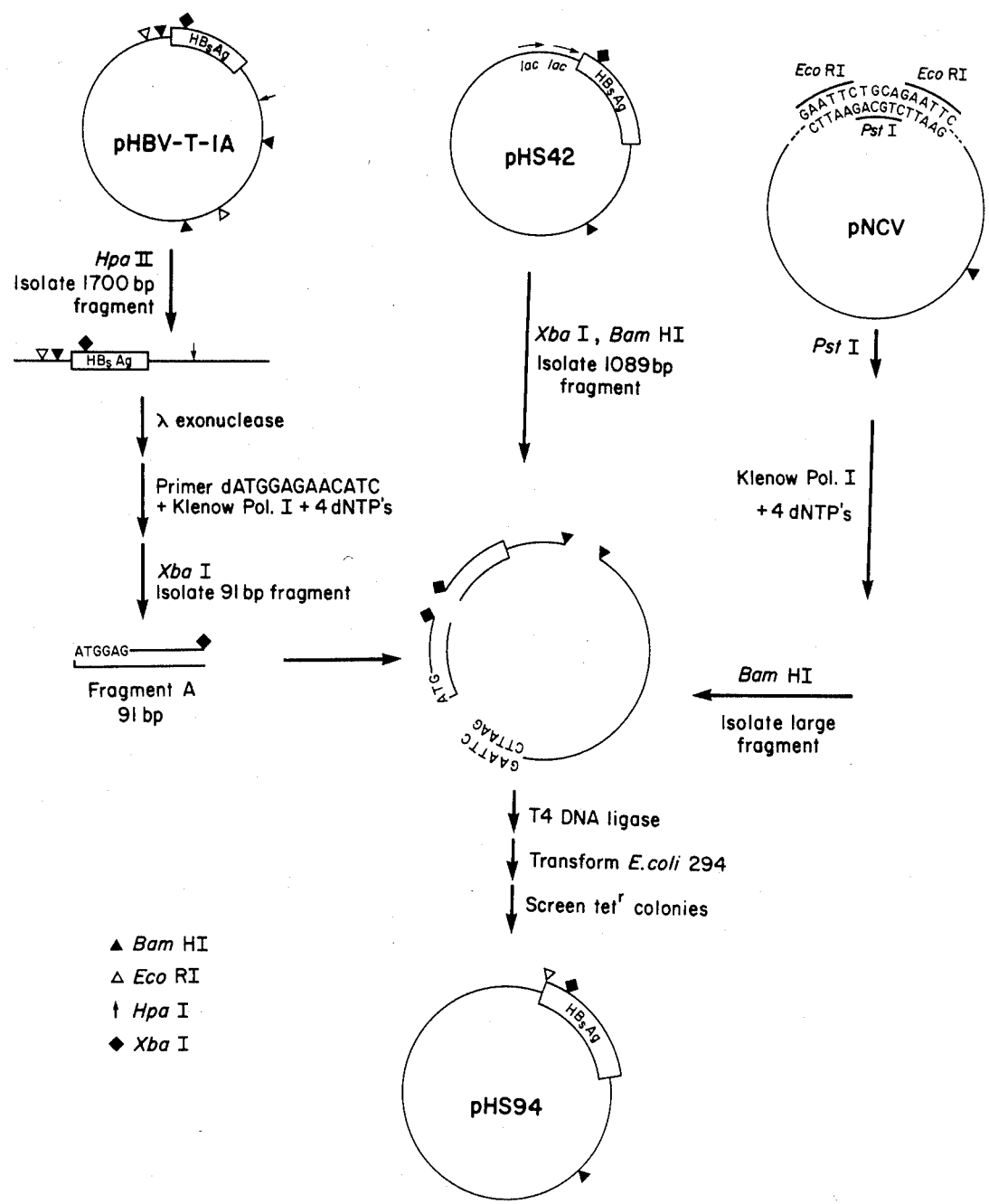
FIG. 2 depicts the construction of plasmid pHS94 harboring HBsAg DNA.

GACGTCTTAA located at the EcoRI site. Incorporated into this synthetic DNA sequence is a PstI site. Ten μg of pNCV DNA was first cut with 24 units of PstI enzyme in a 100 μl reaction mixture and then treated with 2 units E. coli DNA polymerase klenow fragment in 50 μl reaction mixture as described above at 8° C. for 1 hour. The DNA polymerase treatment removed the 4 base-pair 3' overhang created by PstI digestion to leave a blunt ended DNA with an intact EcoRI restriction site giving the fragment B, containing the origin of replication of pBR322. The blunt ended HBsAg gene fragment A, prepared above was ligated to the EcoRI site of fragment B. This was accomplished in a three fragment ligation to create a plasmid pHS94. The third fragment (fragment C) was prepared as follows:

2. The HBsAg gene from the plasmid pHBV-T-1A was cleaved with HpaI at a site distal to the HBsAg gene. The HpaI site was ligated to a EcoRI site of pBR322 previously filled in with DNA polymerase I Klenow fragment (9). This was accomplished by subcloning the derivative of pBR322 to give pHS42. This plasmid was cleaved with XbaI (which cleaves at codon 31) and with BamHI (which cleaves 375 base pairs from the EcoRI site pBR322) to give a DNA fragment containing most of the HBsAg gene, ca. 150 base pairs distal to the HBsAg gene, and the promotor/operator and the first 200 base pairs of the tetracycline resistance gene. The DNA fragment C, bounded by XbaI and BamHI was isolated by PAGE and used in the three fragment ligation described above to give the plasmid pHS94. (FIG. 2).

CONSTRUCTION OF RECOMBINANT SV40 DNA CAPABLE OF SYNTHESIZING HBSAG

Figure 3:
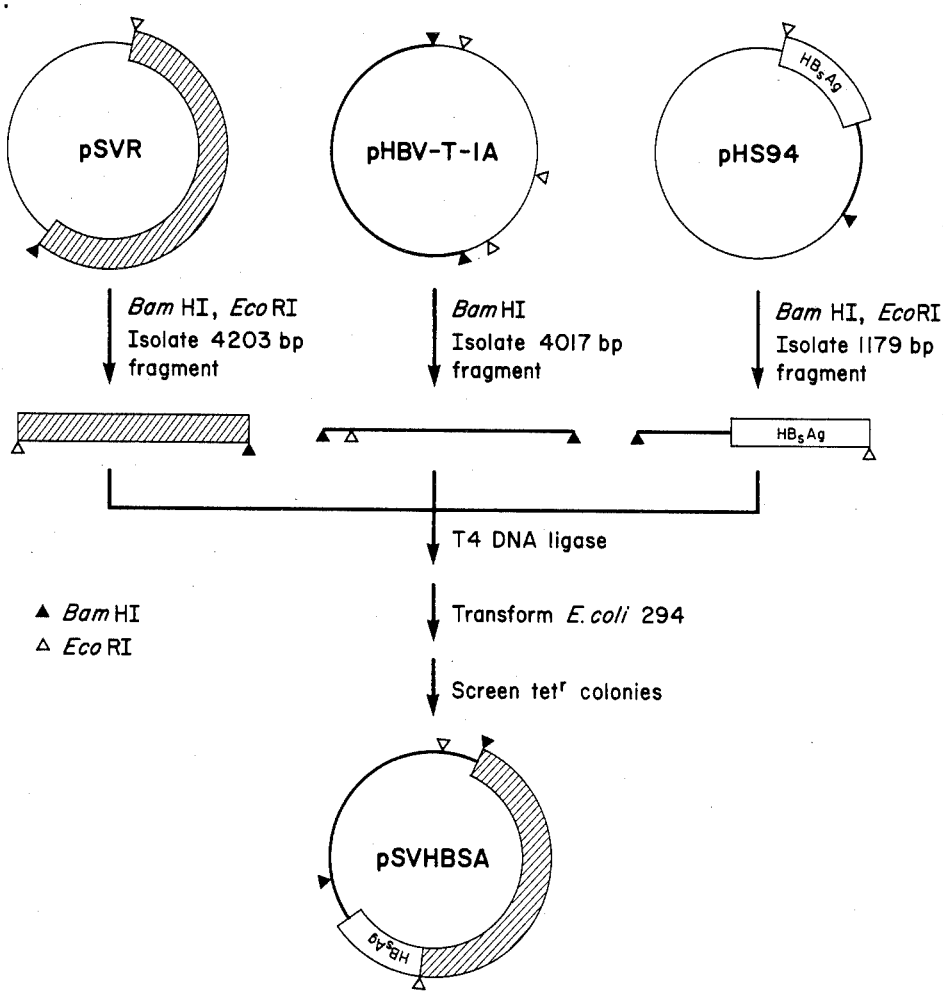
FIG. 3 depicts the construction of plasmid pSVHBSA containing HBsAg DNA and sequences of DNA derived from SV40 and pBR322. In Part B, the DNA sequence surrounding the ATG initiation codon of VP-1 protein (boxed in top line) is compared with that of HBsAg created in the recombinant (boxed ATG in bottom line). The Hind III site which was converted to an EcoRI site is underlined.

To assure that we have large quantities of properly ligated DNA to transfect monkey cells, the ligated DNA was cloned in E. coli in the following manner. As shown in FIG. 3, the BamHI to EcoRI fragment containing SV40 DNA from pSVR was first ligated to the EcoRI to BamHI fragment containing hepatitis surface antigen from pHS94 through its EcoRI site and the resulting fragment was subsequently cloned in the BamHI site of pBR322.

The properly constructed DNA, pSVHBSA, can then be cleaved with restriction endonuclease BamHI to generate a DNA fragment of 5382 nucleotides which consists of a recombinant SV40 genome with the coding region of its VP1 protein replaced by that of the gene encoding hepatitis surface antigen.

For the construction of pSVHBSA DNA, 0.3 μg of the SV40 DNA containing DNA fragment from the BamHI+EcoRI digested pSVR DNA; 50 ng of the pBR322 containing DNA fragment from BamHI digested pHBV-T-IA DNA (see FIG. 2 for detail structure) and 0.2 μg of HBsAg coding sequence containing DNA from BamHI+EcoRI digested pHS94 were ligated by T4 DNA ligase through their respective BamHI and EcoRI sites in a 15 μl ligation mixture in an overnight incubation. One class of proper ligated DNA products has reconstituted an intact tet$^R$ gene of pBR322 and therefore can be selected for by tet$^R$ among large number of tet$^S$ recombinants resulted from self-ligation of vector DNA. The structure of the pSVBSA was then verified by restriction enzyme digestion.

Propagation of Recombinant SV40 Virus and Expression of HBsAg in Monkey Cells To test the efficiency of hepatitis surface antigen synthesis in such a vector system, the BamHI cleaved pSVHBSA DNA was introduced into a monolayer of CV-1 cells (10) by the DEAE dextran method (11) and cells coinfected with either tsA28 or tsA58 viruses (12). The CV-1 cell monolayer was then incubated at 41° C. under proper culture conditions (11). Both tsA28 and tsA58 represent temperature sensitive mutants in the SV40 T antigen and, therefore, cannot multiply at 41° C. (1). Likewise, CV-1 cells which contained only recombinant SV40 genome (pSVHBSA) do not produce infectious virus because pSVHBSA lacks the VP-1 gene. As expected, cytopathic effect was observed after 4 days in the CV-1 cells which contained both ts SV40 virus and the recombinant SV40 genome. Complete cell lysis was observed after 2 weeks of incubation. No cytopathic effect was observed in the CV-1 cells which received only recombinant SV40 genome or ts SV40 virus. Using a commercial radioimmunoassay for HBsAg (13), surface antigen production in the culture medium was detected as early as 4 days after the introduction of DNA. Quantitative assays showed that a monolayer of $1 \times 10^6$ CV-1 cells produced up to 3.8 µg of HBsAg for each infectious cycle, an equivalent of $9 \times 10^7$ molecules/cell. This number is almost identical to the estimated number of SV40 VP-1 protein molecules produced in a single infectious cycle (1).

Figure 7:
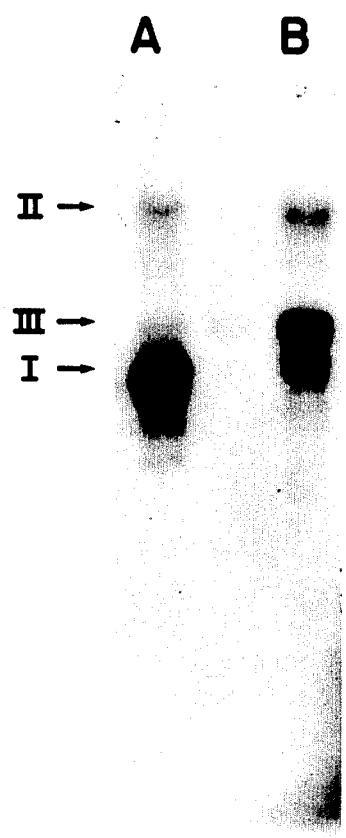
FIG. 7 demonstrates the presence of HBV sequences replicating as part of SV40.

To determine whether the recombinant SV40 genome is packaged and propagated in CV-1 cells as is SV40 virus, a plate of CV-1 cells was infected at 41° C. with ts SV40 virus plus an aliquot of the lysate from the original co-infected cells. Low molecular weight DNA from the infected cell was isolated by the method of Hirt (14) 72 hours post infection. The isolated DNA was either untreated or cleaved with restriction endonucleases and fractionated by gel electrophoresis on agarose. The fractionated DNA was then denatured and transferred to nitrocellulose paper by the method of Southern (15), and probed with $^{32}$P-labelled pHS94 DNA. As can be seen in FIG. 7, the recombinant DNA molecules containing hepatitis gene sequence exist mostly as closed-circular DNA with a size indistinguishable from SV40 viral DNA (lane A). The majority of the recombinant DNA regenerates its BamHI site through in vivo ligation (lane B). As expected, the Bam-EcoRI fragment which contains the coding region of hepatitis B surface antigen (see FIG. 3) can also be isolated in an unaltered form.

A 150 mm plate of CV-1 cells grown to 90 percent confluency was infected with a lysate prepared from an original transfection experiment (which contained both recombinant and tsA28 viruses) and incubated at 41° C. after supplemental with excess tsA28 virus. After 70 hours post-infection, medium was harvested to characterize the HBsAg synthesized. Additionally, intracellular low molecular weight DNA was isolated according to the methods of Hirt (14). The isolated DNA was resuspended in 1 ml of buffer containing Tris-Cl (pH 7.4), 1mM EDTA.

Five µl of uncut DNA, and 5 µl of BamHI digested DNA, was then fractionated by electrophoresis through a 0.8 percent agarose gel in TBE Buffer, along with SV40 DNA treated similarly as a control. The DNA pattern on the gel was transferred to a sheet of nitrocellulose paper and hybridized to $^{32}$P-labelled pHS94 DNA (15), as a source of HBsAg gene probe. FIG. 7 represents the autoradiographic image of $^{32}$P-labelled pHS94 DNA after hybridization. Lanes A and B are untreated Hirt supernatant and BamHI digested Hirt supernatant DNA respectively. I, II and III denote the position of form I, form II and form III of control SV40 DNA whose positions were determined by ethidium bromide staining before DNA was transferred to nitrocellulose paper.

Figure 8:
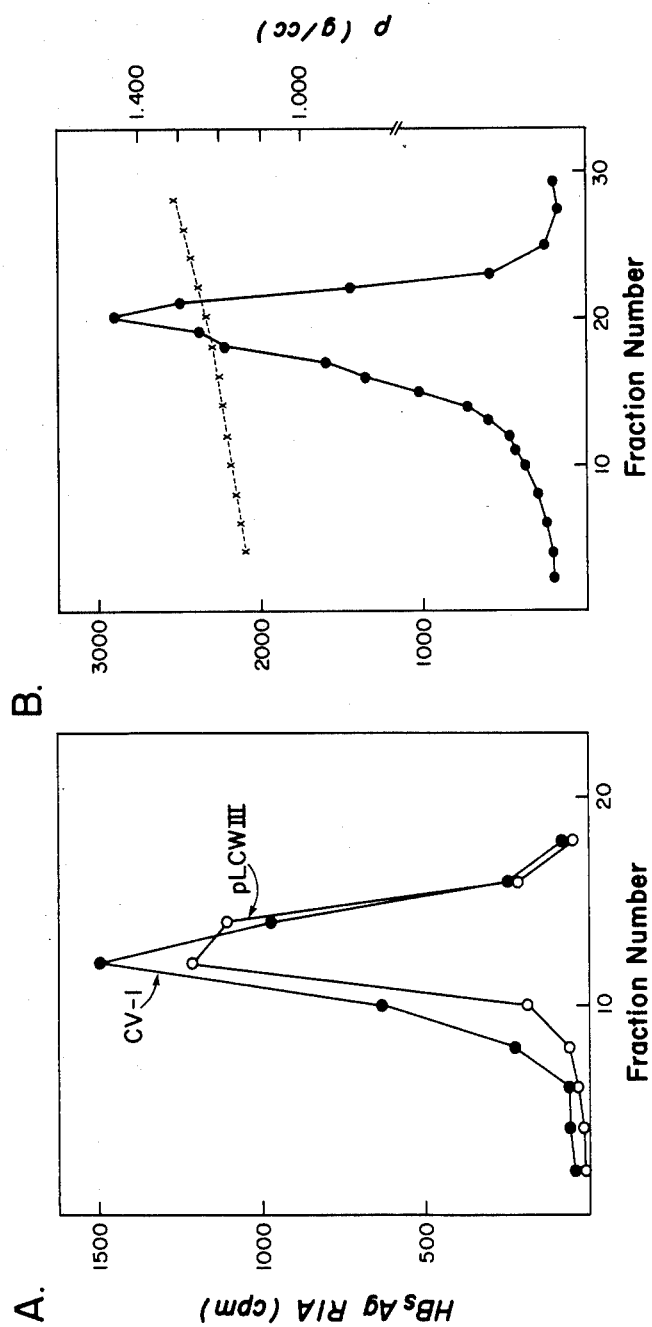
FIG. 8A depicts a sucrose gradient sedimentation of HBsAg synthesized via the recombinant vector hereof.
FIG. 8B is a corresponding CsCl gradient centrifugation thereof.
Figure 9:
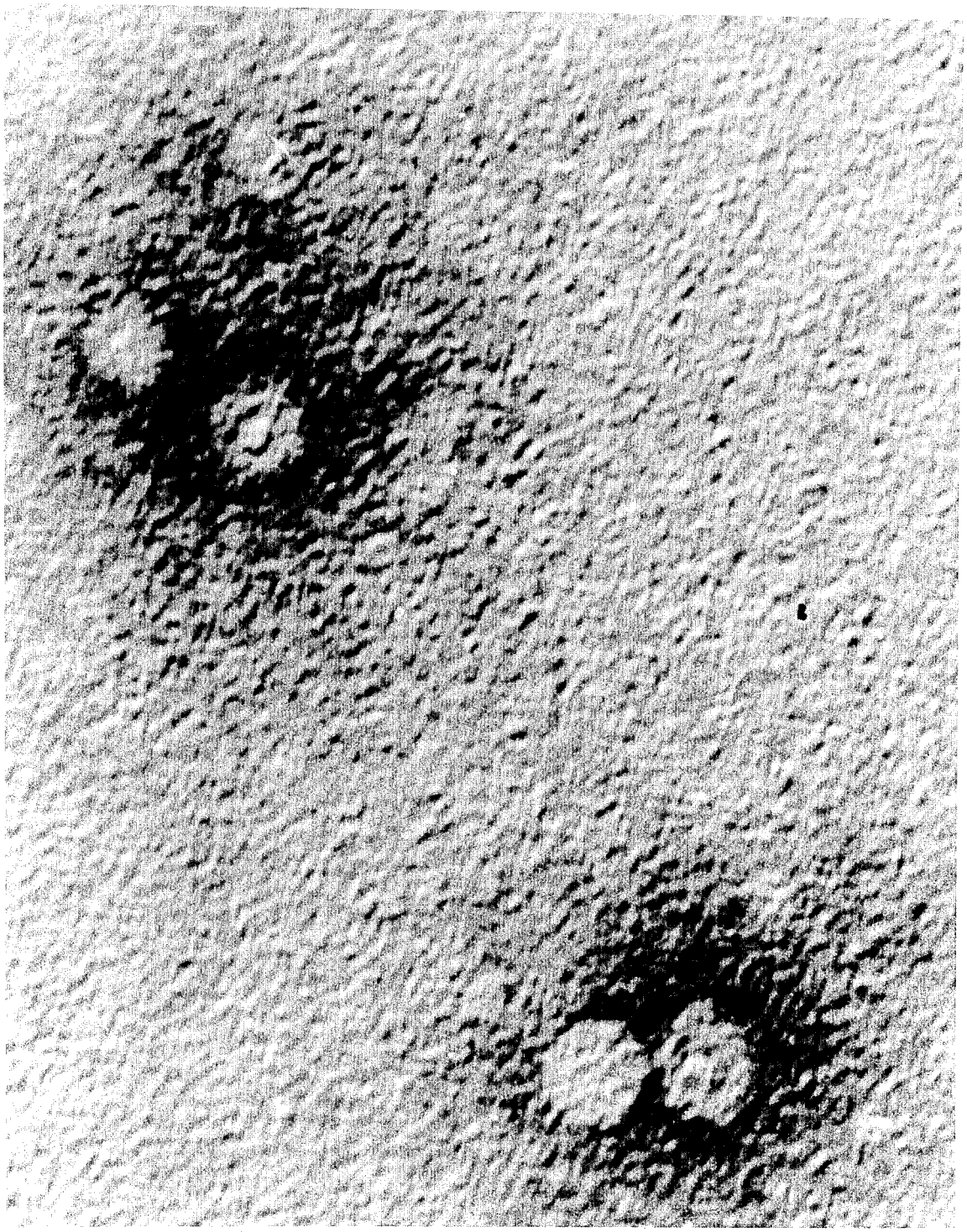
FIG. 9 depicts an electron micrograph of HBsAg synthesized as a 22 nm particle in accordance with this invention.

Hepatitis Surface Antigen Encoded by PSVHBSA is Synthesized in a Particle Form Hepatitis surface antigen is synthesized and secreted from infected liver cells as a particle (6). Sequence analysis of various cloned hepatitis DNA suggests the possibility that the mature surface antigen may be cleaved from a larger precursor protein (8). Since only DNA encoding the mature HBsAg molecule, plus some 3' untranslated sequences, are incorporated into the SV40 genome in the construction described, it can be asked whether the speculated precursor-peptide plays any functional role in assembling the 22 nm particle and in its eventual secretion from the cell. To this end, the synthesized hepatitis surface antigen has been characterized by comparing its property with authentic protein through sedimentation velocity, sedimentation equilibrium, and electron microscopic analysis. As shown in FIG. 8, the hepatitis surface antigen synthesized in this vector system has a sedimentation rate indistinguishable from hepatitis surface antigen isolated from the medium of an infected liver cell line (17) and has a buoyant density of 1.22 g/cm$^3$, again similar to an authentic surface antigen 22 nm particle (6). Examination by electron microscopy of purified surface antigen has also revealed a predominant particulate structure with a mean diameter of 220 Å (22 nm), morphologically identical to authentic 22 nm particles (FIGS. 8 and 9). Therefore, the mature hepatitis surface antigen protein monomer is the only essential structural component encoded by hepatitis virus which is required for the assembly of the 22 nm particle.

A. Comparison of the sedimentation velocity of HBsAg synthesized in CV-1 cells and that of HBsAG synthesized and secreted by a Hepatoma cell line PLC (17 and 18). (FIG. 8A). Culture medium harvested from the experiment described in FIG. 7 was the source of HBsAg used in this experiment. HBsAg produced by the PLC cell line (17 and 18) was harvested from the culture medium. HBsAg from both cultures was first precipitated by ammonium sulfate at 45 percent saturation and resuspended (at a final concentration of HBsAg of 0.5 µg/ml) in a buffer containing 20 mM tris-Cl (pH 7.4), 0.5 mM EDTA and 0.5 mM NaCl. 200 µl of each sample was loaded on two parallel 5 ml sucrose gradients (5–20 percent sucrose) in the same buffer. Centrifugation was carried out at 45,000 rpm in a Beckman SW 50.1 rotor for 80 minutes at 4° C. HBsAg was detected using the commercial HBsAg assay kit (Austria II-125, Abbott Lab). Recovery of HBsAg was invariably greater than 80 percent.

B. Buoyant density determination of HBsAg synthesized in CV-1 cells. (FIG. 8B). 2 µg of HBsAg from pooled infected culture medium were precipitated by ammonium sulfate at 45 percent saturation, fractionated over an agrose gel permeation column (A 5.0 M. Bio-Rad), and then sedimented through a 5–20 percent sucrose gradient as described in A. After sucrose gradient centrifugation, pooled HBsAg was dialyzed against gradient buffer without sucrose, and solid CsCl was then added to give the solution (7 ml) a final density of 1.2 g/c.c. It was then centrifuged at 50,000 rpm in a Sorvall T 865.1 rotor for 68 hours. Assays were performed as described in A. Recovery of HBsAg in CsCl gradients was about 70 percent. Peak fractions were then pooled, dialyzed against 10 mM TrisCl, 100mM NaCl and 0.5 mM EDTA buffer, concentrated, and prepared for electron microscopic examination.

To prepare the antigen for electron micrographs, carbon coated copper grids were prepared. One drop of buffer containing HBsAg protein (1 μg/ml) was placed on a grid for 30 min. at room temperature. The protein solution was blotted off the grid radially and washed once with 4 drops of $H_2O$. The grid was then stained with 1.0 percent Na-phosphotungstate, pH 7.6, for one minute, and dried with filter paper. Electron micrographs were taken on a Phillips E. M. 400 at magnification 77700. This provided a negative from which a positive picture was made by enlargement (ca. 10 times) as depicted in FIG. 9.

Construction of non-Lytic Vectors Expressing HBsAg

Recombinant plasmids were assembled which contain pBR322 sequences derived from the plasmid pML (21). 348 base-pairs of SV40 DNA which comprise the origin region of DNA replication as well as the promoter sequences for both the early and late transcriptional units, and HBV sequences which encode the gene for HBsAg. The origin of SV40 was isolated by digesting SV40 DNA with HindIII, and converting the HindIII ends to EcoRI ends by the addition of a converter (AGCTGAATTC). This DNA was cut with PvuII, and RI linkers added. Following digestion with EcoRI, the 348 base-pair fragment spanning the origin was isolated by polyacrylamide gel electrophoresis and electroelution, and cloned in pBR322. Expression plasmids pHBs348-E and pHBs348-L were constructed by cloning the 1986 base-pair fragment resulting from EcoRI and BglII digestion of HBV (22) (which spans the gene encoding HBsAg) into the plasmid pML (21) at the EcoRI and BamHI sites. (pML is a derivative of pBR322 which has a deletion eliminating sequences which are inhibitory to plasmid replication in monkey cells (21)). The resulting plasmid (pRI-Bgl) was then linearized with EcoRI, and the 348 base-pair fragment representing the SV40 origin region was introduced into the EcoRI site of pRI-Bgl). The origin fragment can insert in either orientation. Since this fragment encodes both the early and late SV40 promoters in addition to the origin of replication, HBV genes could be expressed under the control of either promoter depending on this orientation (pHBS348-E representing HBs expressed under control of the early promoter; pHBs348-L representing HBs expressed under control of the late promoter).

Replication of SV40-HBV Plasmids in Monkey Cells

Figure 4:
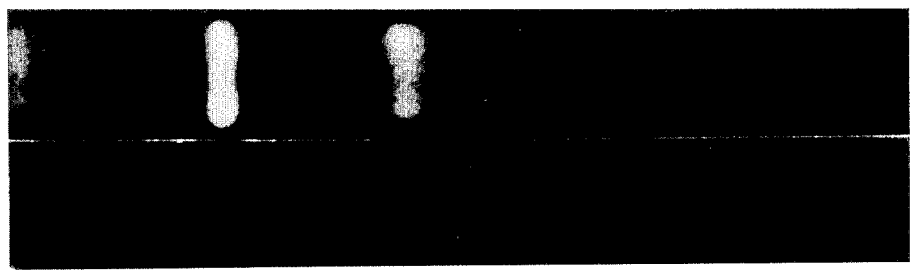
FIG. 4 depicts the replication of plasmid DNA in monkey cells. Monolayers of Cos cells were grown to 50–60 percent confluency in 6-cm plastic dishes. The cells were washed with Dulbecco's modified medium, and 2 ml of medium containing 1 µg of plasmid DNA and DEAE-dextran at 200 µg was applied for 12 hours at 37°. The DNA solution was removed, the cells washed once with medium, and 5 ml of medium containing 10 percent fetal calf serum was added and the cells incubated at 37° for either one or three days prior to DNA extraction. At these times, small supercoiled plasmid DNA was isolated according to the method of Hirt (14). The DNA was subjected to agarose gel electrophoresis and transferred to nitrocellulose (15). To visualize replicating plasmids, the nitrocellulose filter was probed with P32 labelled HBV DNA. Lanes (a) - DNA from Hirt lysates of cells transfected with pRI-Bgl. Lanes (b) - DNA from Hirt lysates of cells transfected with pHBs348-L. Lane (M) - 1 µg of pHBs348-L DNA. Arrows refer to location of closed circular DNA (I) and open circular DNA (II).
Figure 4:
Figure 4:
Figure 4:

The replication of HBV-SV40 recombinant plasmids in the COS-7 line of monkey cells was demonstrated as follows: At various times following DNA transfection by the DEAE-dextran technique, low molecular weight DNA was isolated by the method of Hirt (14), fractionated by electrophoreis in agarose gels and analyzed by Southern blot hybridization (15). FIG. 4 demonstrates that immediately following transfection, little or no supercoiled plasmid is present in COS cells. Three days after transfection, however, extensive replication of the input DNA has occurred, following introduction of either pHBs348-L DNA (lane b) or pHBs348-E DNA. As expected, no plasmid replication is observed following transfection of plasmid pRI-Bgl (which lacks the SV40 origin sequences but is otherwise identical to the above expression plasmids) (lanes a).

Synthesis of HBsAG in Monkey Cells Transfected With Recombinant Plasmids

Figure 5:
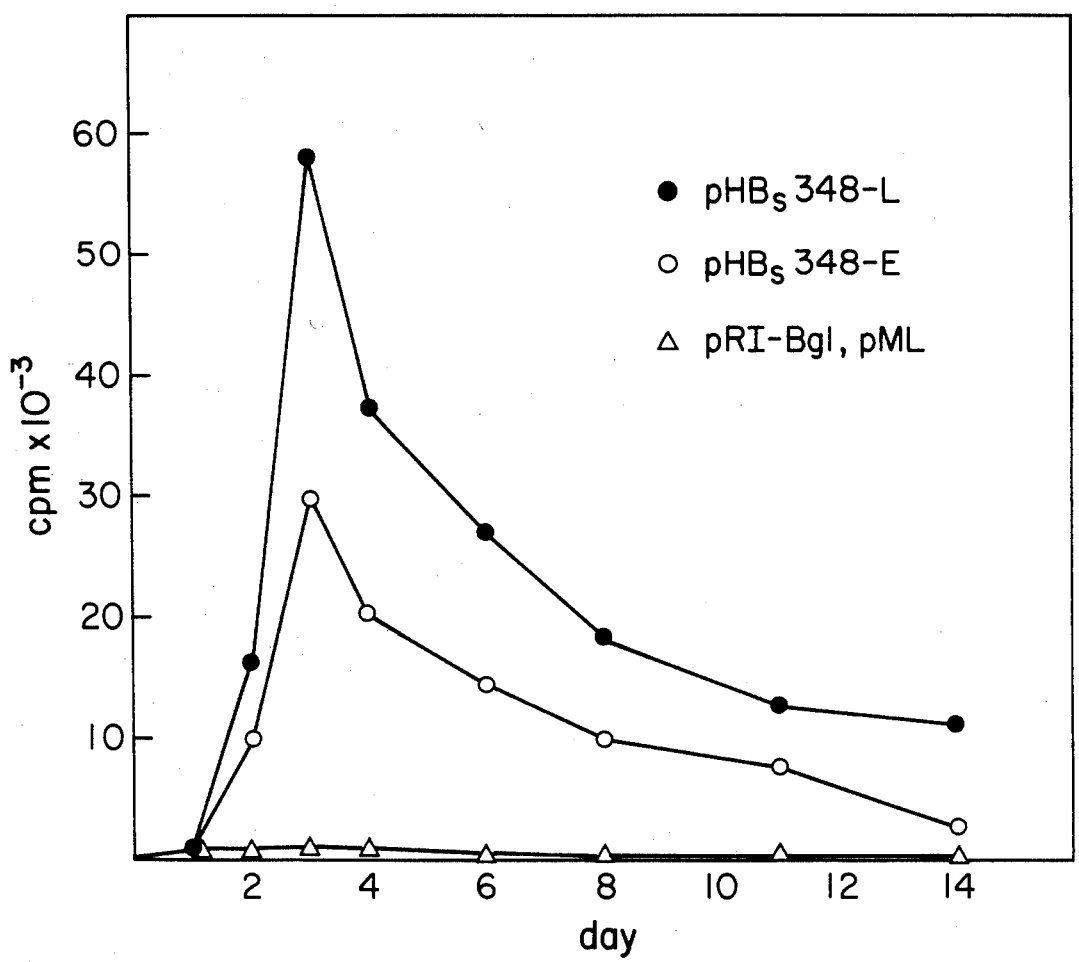
FIG. 5 depicts quantitation of HBsAg synthesized by recombinant plasmids in Cos cells. Monolayers of Cos cells were grown to approximately 50 percent confluency in 6-cm plastic dishes, and prepared for DNA transfection as described in FIG. 4. 2 ml of Dulbecco's modified medium containing 10 percent fetal calf serum was added following transfection, and the medium assayed at various times for HBsAg expression following 24 hours accumulation. HBsAg expression is expressed as counts per minute (cpm) in 0.2 ml undiluted medium, as assayed by RIA (Abbott Labs).

Plasmids pML, pRI-Bgl, pHBs348-E and pHBs348-L were introduced into the COS-7 line of monkey cells (23), modifying the DEAE-dextran procedure (11) by increasing the time of treatment and exposure of the cells to DEAE-dextran and DNA to 12 hours. The COS-7 cells line harbors an integrated copy of the early region of SV40 and expresses constitutively the SV40 A gene product (T antigen). Plasmids containing a functional origin of SV40 DNA replication have been demonstrated to replicate in monkey cells in the presence of SV40 T antigen (20, 21). FIG. 5 demonstrates that COS cells transfected with plasmids pHBs348-E and pHBS348-L begin expressing significant quantities of HBsAg by day 2, and continue expressing beyond a two-week period. The level of expression directed by pHBs348-L is somewhat higher than that directed by pHBs348-E. One interpretation of these results is that the late SV40 promoter may be more effective than the early promoter in this system.

Tissue Culture Drived HBsAG is Immunogenic in Animals

Figure 6:
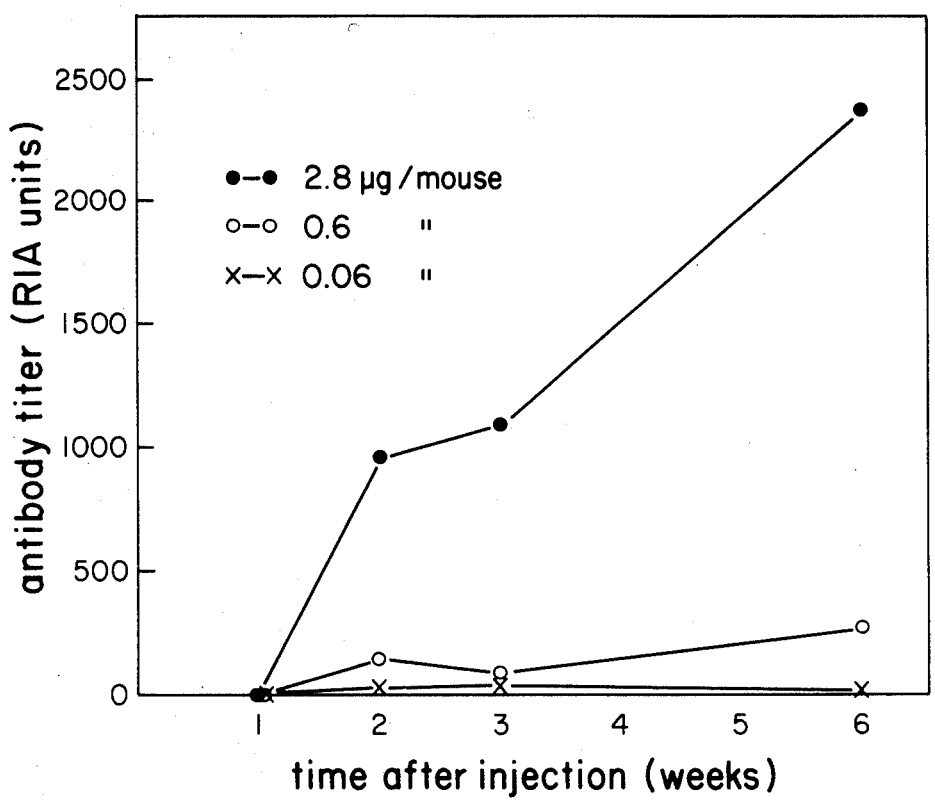
FIG. 6 depicts immunogenicity of HBsAg derived from monkey cells. Medium from 20 15-cm dishes of Cos cells transfected with pHBs348-L was harvested and HbsAg purified as described above for electron microscopic examination. Three groups of five mice were immunized with 2.8 µg, 0.6 µg, or 0.006 µg of purified HBsAg in the presence of complete Freund's adjuvant. Control mice were immunized with similar amounts of authentic HBsAg derived from human serum (North American Biologicals Inc.) Mice were tail bled at various times following immunization, anti-HBsAg antibody quantitated by RIA (Abbott Labs), and the results expressed as the average titer per mouse. Mice immunized with HBsAg derived from tissue culture developed titers identical to mice immunized with HBsAg derived from human serum.

Having demonstrated that tissue culture derived particles of HBsAg are antigenically active, it was desired to determine whether these particles are immunogenic in animals. Therefore, the antigen produced by COS-7 cells was purified by a combination of ammonium sulfate precipitation, sucrose gradient centrifugation, and CsCl density gradient centrifugation. Tissue culture-derived HBsAg was injected into each mouse, while control mice were immunized with identical quantities of commercially available HBsAg (North American Biologicals Inc.) derived from human serum. Titers of anti-HBsAg were then determined at various times following immunization. FIG. 6 illustrates that significant titers of anti-HBsAg appeared in mice immunized with authentic HBsAg as well as in mice immunized with tissue culture derived HBsAg. In addition, the kinetics and titers of anti-HBsAg antibody appearance in mice immunized with tissue culture derived HBsAg were indistinguishable from those observed in mice immunized with authentic HBsAg. We therefore conclude that HBsAg synthesized in monkey cells by recombinant DNA techniques is similar, if not identical, in immunogenicity to HBsAg derived from human serum, whose effectiveness as a vaccine has been amply demonstrated.

Pharmaceutical Compositions

The compounds of the present invention can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Science* by E. W. Martin, which is hereby incorporated by reference. Such compositions will contain an effective amount of the polypeptide product hereof together with a suitable amount of carrier vehicle in order to prepare pharmaceutically acceptable compositions suitable for effective adminitration to the host. One preferred mode of adminstration is parenteral. Suitable animal health formulations are prepared as in the case of pharmaceutical compositions, mutatis mutandis.

Vaccine Preparation

The vaccines of the present invention, incorporating a suitable polypeptide produced as herein described, can be prepared according to known methods, wherein said polypeptide is combined in admixture with a suitable vehicle. Suitable vehicles include, for example, saline solutions, various known adjuvants, or other additives recognized in the art for use in compositions applied to prevent viral infections. Such vaccines will contain an effective amount of the polypeptide hereof and a suitable amount of vehicle in order to prepare a vaccine useful for effective administration to the host. Attention is also directed to *New Trends and Developments in Vaccines,* Editors: A. Voller and H. Friedman, University Park Press, Baltimore, 1978, which is hereby incorporated by reference, for further background details on the preparation of vaccines.

Because of the unique methods by which the active component of these vaccines are produced, vaccines hereof are likely to be substantially free of extraneous protein(s) and of other viral and cellular components. Therefore, they are less likely to produce the complications of whole killed or attenuated virus vaccine preparations.

It will be apparent to those skilled in the art in the light of the foregoing discussion that the invention, such as in the selection of intended polypeptide product, is not to be limited to the preferred embodiments hereof but rather only to the lawful scope of the appended claims.

BIBLIOGRAPHY

1. N. H. Acheson in *Molecular Biology of Tumor Viruses.* (J. Tooze ed.) Cold Spring Harbor Lab. N.Y. 2nd edi. Part 2. pp. 125–204 (1980).
2. R. Crea, et al., *Proc. Natl. Acad. Sci. (U.S.A.)* 75, 5765 (1978).
3. D. V. Goeddel, et al., *Proc. Natl. Acad. Sci. (U.S.A.)* 76, 106 (1979).
4. R. W. Davis, et al., *Advanced Bacterial Genetics,* Cold Spring Harbor Laboratory, N.Y. pp. 116–125 (1980).
5. D. H. Hamer and P. Leder, *Cell,* 18, 1299 (1979).
6. O. Blumberg, *Science* 197, 19 (1977).
7. P. Valenzuela, et al., *Nature,* 280, 815 (1979).
8. P. Charney et al., *Proc. Natl. Acad. Sci. (U.S.A.)* 76, 2222 (1979).
9. H. Jacobsen et al., *Eur. J. Biochem.* 45, 623 (1974).
10. J. E. Mertz and P. Berg., *Virology,* 62, 112 (1974).
11. J. H. McCutchan and J. S. Pagano, *J. Nat. Cancer Inst.* 41, 351 (1968).
12. P. J. Tegtmeyer, *J. Virology* 10, 591 (1972).
13. Ausria II-125. Abbott Lab.
14. B. J. Hirt, *J. Mol. Biol.* 26, 365 (1967).
15. E. M. J. Southern, *J. Mol. Biol.* 98, 503 (1975).
16. C-J. Lai and D. Nathans, *J. Mol. Biol.* 89, 179 (1974).
17. J. J. Alexander et al., *S. Afr. Med. J.* 50, 2124 (1976).
18. P. L. Marion et al., *J. of Virol.* 32, 796 (1979).
19. *DNA Tumor Viruses* 2nd Ed. (Ed. J. Tooze), Cold Spring Harbor Lab., N.Y. (1980).
20. Myers and Tjian, *Proc. Natl. Acad. Sci. (U.S.A)* 77, 6491 (1980).
21. Lusky and Botchan, *Nature* 293, 79 (1981).
22. *Animal Virus Genetics* (Ed. Fields, Jaenisch and Fox), Chapter 5, p 57, Academic Press, N.Y. (1980).
23. Gluzman, *Cell* 23, 175 (1981).

We claim:

1. A vaccine comprising a pharmaceutically acceptable vehicle and hepatitis B surface antigen particle having a diameter of about 22 nm, the hepatitis B surface antigen in the particle consisting of mature hepatitis B surface antigen.

* * * * *